US012797228B2

(12) United States Patent
Watchmaker et al.

(10) Patent No.: US 12,797,228 B2
(45) Date of Patent: Nov. 17, 2026

(54) ANGULAR DIGITAL ORTHOSIS FOR LOSS OF DISTAL JOINT EXTENSION

(71) Applicants: Greg Watchmaker, Mequon, WI (US); Randy Dahl, Sussex, WI (US)

(72) Inventors: Greg Watchmaker, Mequon, WI (US); Randy Dahl, Sussex, WI (US)

( * ) Notice: Subject to any disclaimer, the term of this patent is extended or adjusted under 35 U.S.C. 154(b) by 0 days.

(21) Appl. No.: 19/567,158

(22) Filed: Mar. 15, 2026

(65) Prior Publication Data

US 2026/0207368 A1 Jul. 23, 2026

Related U.S. Application Data

(63) Continuation-in-part of application No. 18/233,169, filed on Aug. 11, 2023, now Pat. No. 12,685,659.

(51) Int. Cl.
*A61F 5/058* (2006.01)

(52) U.S. Cl.
CPC ................................ *A61F 5/05875* (2013.01)

(58) Field of Classification Search
CPC ........ A61F 13/12; A61F 13/104; A61F 5/058; A61F 5/05875; A61F 5/0118; A61F 5/10; A61F 5/102; A61F 5/50
USPC ................. 128/869, 879, 880; 602/5, 22, 61
See application file for complete search history.

(56) References Cited

U.S. PATENT DOCUMENTS 681,054 A 8/1901 Hawley
2,548,378 A 4/1951 Kleinfeld
3,039,460 A 6/1962 Chandler
4,441,489 A * 4/1984 Evans ................. A61F 5/05875 602/22
D293,379 S 12/1987 Link
5,183,458 A * 2/1993 Marx ........................ A61F 5/10 602/30
5,197,943 A * 3/1993 Link ................... A61F 5/05875 2/21
5,848,983 A 12/1998 Basaj
6,692,452 B2 2/2004 Chow
D515,216 S 2/2006 Weber
D715,951 S 10/2014 Stuart
9,358,148 B2 6/2016 Barnes
D799,710 S 10/2017 Wong
9,872,796 B1 1/2018 Karna
2009/0099493 A1 4/2009 Barnes
2009/0204044 A1* 8/2009 Benison .............. A61F 5/05875 602/22
2019/0008688 A1* 1/2019 Stojanovski ...... A61F 13/00063
2022/0039992 A1 2/2022 Bacik
2025/0049605 A1* 2/2025 Watchmaker ....... A61F 5/05875

FOREIGN PATENT DOCUMENTS

WO WO-2021246962 A1 * 12/2021 ......... A61F 5/05883

* cited by examiner

*Primary Examiner* — Caitlin A Carreiro

(57) ABSTRACT

Embodiments of the inventive concepts disclosed herein are directed to an angular digital device for loss of distal joint extension. A device formed from a thin, rigid material shaped to fit the dorsal soft-tissue contour of the middle phalanx of a digit with one or more apex volarly angled distal projections which arise at the level of the distal interphalangeal joint and with a thin sling of material secured to the distal projection(s) by which the volar pad of the distal phalanx is supported in order to provide hyperextension of the distal joint of the digit while maintaining tactile function of the pad of the digit.

9 Claims, 7 Drawing Sheets

ANGULAR DIGITAL ORTHOSIS FOR LOSS OF DISTAL JOINT EXTENSION

CROSS-REFERENCE TO RELATED APPLICATIONS

This application is a continuation-in-part of U.S. application Ser. No. 18/233,169, filed Aug. 11, 2023, the entirety of which is incorporated herein by reference.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A READ-ONLY OPTICAL DISC, AS A TEXT FILE OR AN XML FILE VIA THE PATENT ELECTRONIC SYSTEM

Not Applicable

STATEMENT REGARDING PRIOR DISCLOSURES BY THE INVENTOR OR A JOINT INVENTOR

Not Applicable

BACKGROUND OF THE INVENTION

This invention belongs to a class of devices that treat injuries of the distal joint of the digit wherein there is loss of extension of the distal interphalangeal joint (DIP) commonly referred to as a mallet injury. These devices passively maintain the DIP joint in extension during healing of the terminal tendon in a finger or extensor pollicis longus tendon in a thumb.

Previously described devices in this class decrease tactile function of the digit while being worn by virtue of their designs which wrap around the tip of the digit (Barnes 2009, Barnes 2016), or cover a portion of the skin of the finger pad with a rigid or dense material (Kleinfield 1949, Link 1987, Link 1993, Stuart 2014, Wong 2017).

The current invention is novel by overcoming the loss of tactile function of the skin of the finger pad created by these prior designs. The current invention does so by leaving the tip of the digit uncovered by any material of the device and also by using a thin, flexible material as the element of the splint which contacts the finger pad.

Prior designs are limited by the manner in which they cross the DIP joint without an apex volarly angled element at the level of the joint (Hawley 1901, Kleinfeld 1949, Link 1987, Stuart 2014). Such straight designs allow the DIP joint to partially flex if the splint migrates distally while being worn. This is a common problem when perspiration reduces adhesion of the tape or strap used to secure the splint to the middle phalanx. Straight designs or designs with a gentle bow rather than an angle placed at the level of the joint also allow the DIP joint to flex if the splint does not perfectly fit the size of the digit. The additional room within the splint or distal migration of the splint compromises the intended purpose of maintaining full extension or hyperextension of the DIP joint. Additionally prior designs that purposely place the DIP joint in flexion rather than extension are not intended for treatment of mallet injuries (Chandler 1962).

The current invention overcomes prior straight designs by incorporating an apex volar angle to the splint as it crosses the level of the DIP joint. The fixed volar angle of the current invention provides a means for the wearer to achieve a reproducible hyperextension angle across the joint and does not require manipulation of springs or screws as described in prior designs to achieve a desired extension angle.

BRIEF SUMMARY OF THE INVENTION

In one aspect, the embodiments for the inventive concepts disclosed herein are directed to:

A device formed from a thin, rigid material curved to fit the dorsal soft-tissue contour of the middle phalanx of a digit with one or more apex volarly angled distal projections which arise at the level of the distal interphalangeal joint and with a thin sling of material secured to the distal projection (s) by which the volar pad of the distal phalanx is supported in order to provide hyperextension of the distal joint of the digit while maintaining tactile function of the pad of the digit and not encumbering the proximal interphalangeal joint.

BRIEF DESCRIPTION OF THE SEVERAL VIEWS OF THE DRAWING(S)

Implementations of the inventive concepts disclosed herein may be better understood when consideration is given to the following detailed description thereof. Such description makes reference to the included drawings, which are not necessarily to scale, and in which some features may be exaggerated and some features may be omitted or may be represented schematically in the interest of clarity. Like reference numerals in the drawings may represent and refer to the same or similar element, feature, or function. In the drawings.

Figure 5A:
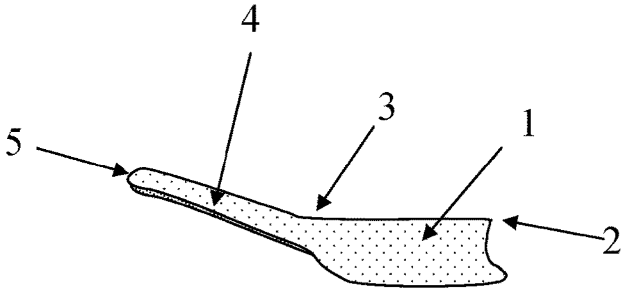
Figure 5B:
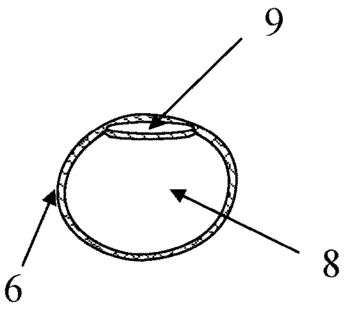
Figure 5C:
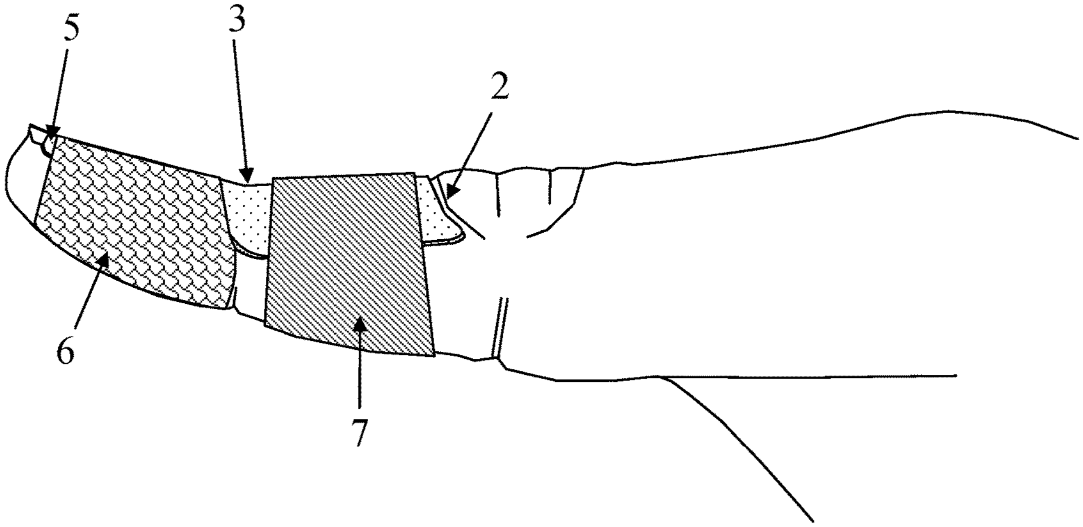

FIG. 5A is a side view drawing of an additional embodiment with a single distal extension. FIG. 5B is a cross-section view illustrating a thin, flexible material of a shape configured to fit the distal aspect of a digit and with a dorsal, longitudinal pocket configured to be fitted over the distal aspect of the embodiment of FIG. 5A. FIG. 5C is a side view drawing of the embodiment, wherein the pocket on the dorsum of the thin, flexible material has been slid over the distal aspect of the embodiment of FIG. 5A, and the embodied device is donned upon a digit.

Figure 6A:
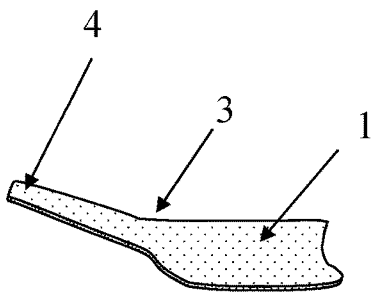
Figure 6B:
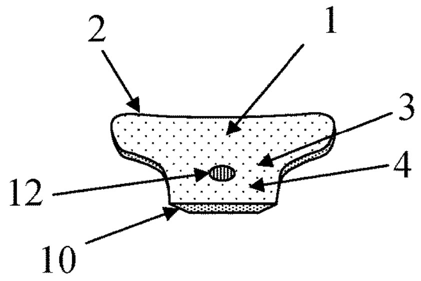
Figure 6C:
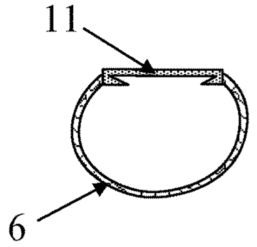
Figure 6D:
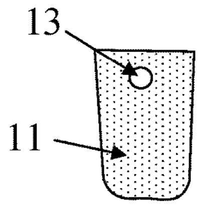
Figure 6E:
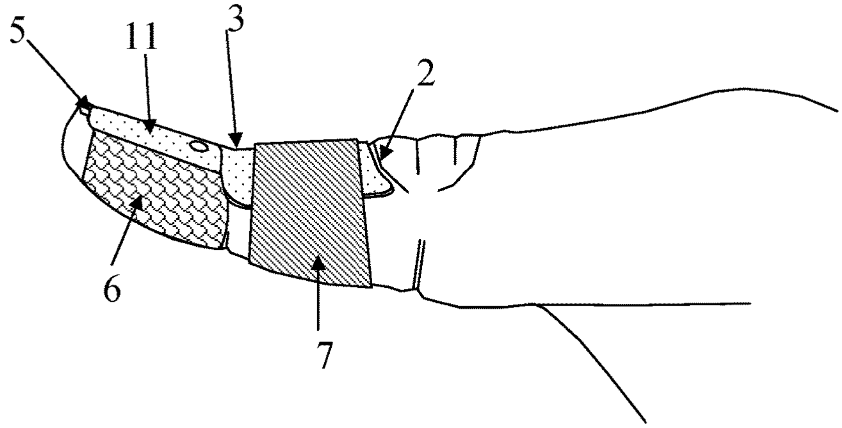

FIGS. 6A-E illustrate the construction of an additional embodiment of the inventive concepts disclosed herein. FIG. 6A illustrates a side view of the first step of construction of this embodiment. FIG. 6B illustrates an end-on view from distal to proximal of the embodiment shown in FIG. 6A. FIG. 6C illustrates a cross-section view illustrating a thin, flexible material of a shape configured to fit the distal aspect of a digit secured to an intermediate rigid component. FIG. 6D illustrates a top view of the intermediate component. FIG. 6E illustrates the thin, flexible material engaged to the proximal rigid component by means of the intermediate component and shown in side view donned upon a digit.

Figure 7A:
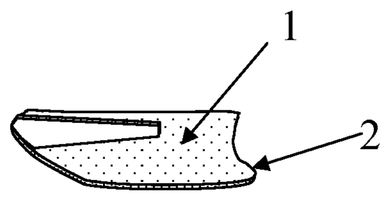
Figure 7B:
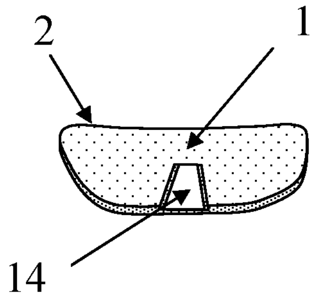
Figure 7C:
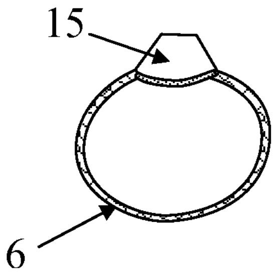
Figure 7D:
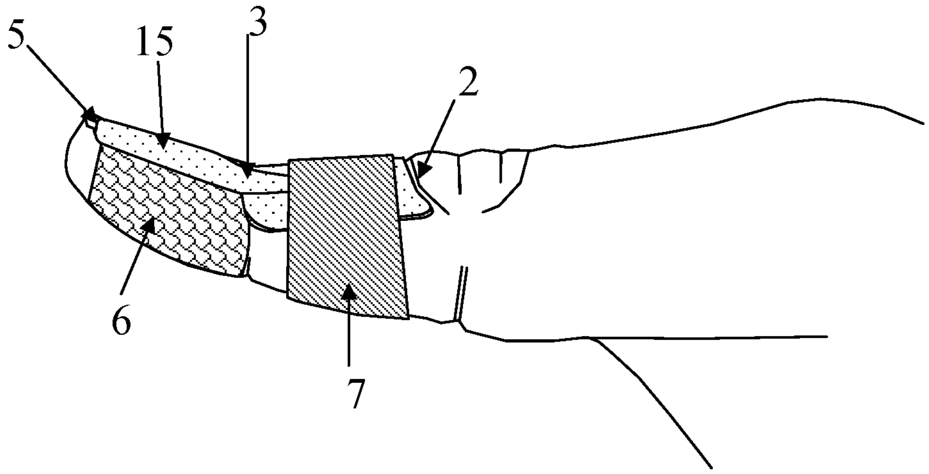

FIG. 7A-7D illustrate the construction of an additional embodiment of the inventive concepts disclosed herein wherein the proximal rigid component of FIG. 7A is illustrated in side view. FIG. 7B illustrates the proximal rigid component on end view. FIG. 7C illustrates a cross-section view of a thin, flexible material of a shape configured to fit the distal aspect of a digit secured to an intermediate rigid component. FIG. 7D illustrates the components of FIGS. 7B and 7C engaged to create the finished device and shown in side view donned upon a digit.

DETAILED DESCRIPTION OF THE INVENTION

Before describing in detail embodiments of the inventive concepts disclosed herein, it should be observed that the inventive concepts disclosed herein include but are not limited to a novel structural combination of components and circuits, and not to the particular detailed configurations thereof. Accordingly, the structure, methods, functions, control and arrangement of components and circuits have, for the most part, been illustrated in the drawings by readily understandable block representations and schematic diagrams, in order not to obscure the disclosure with structural details which will be readily apparent to those skilled in the art, having the benefit of the description herein. Further, the inventive concepts disclosed herein are not limited to the particular embodiments depicted in the schematic diagrams, but should be construed in accordance with the language in the claims.

The device may be used for loss of extensor tendon function of the distal joint of a digit whereby loss of normal motion compromises function. The essential functions of the various embodiments of the device are to provide an extension rotational force centered at the level of the distal interphalangeal joint.

The various elements of the device function through the construction of a thin rigid proximal component contoured to the middle phalanx and one or more apex volar angulated distal extensions to which a thin, flexible material is secured which provides volar support to the pad of the digit.

Figure 1:
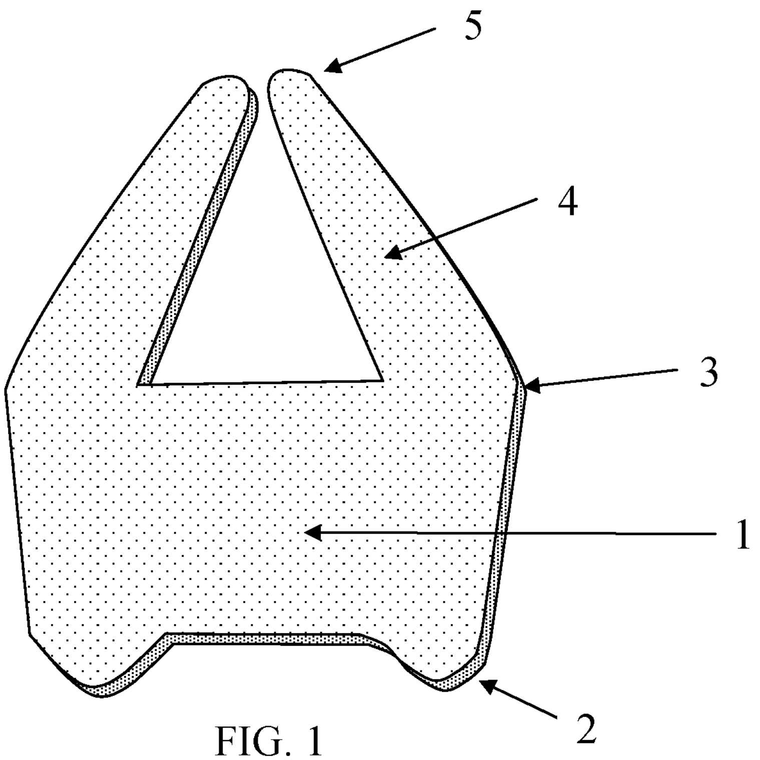
FIG. 1 is a top view drawing of the first step in constructing an angular digital device for the distal interphalangeal joint with some embodiments of the inventive concepts disclosed herein.
Figure 2:
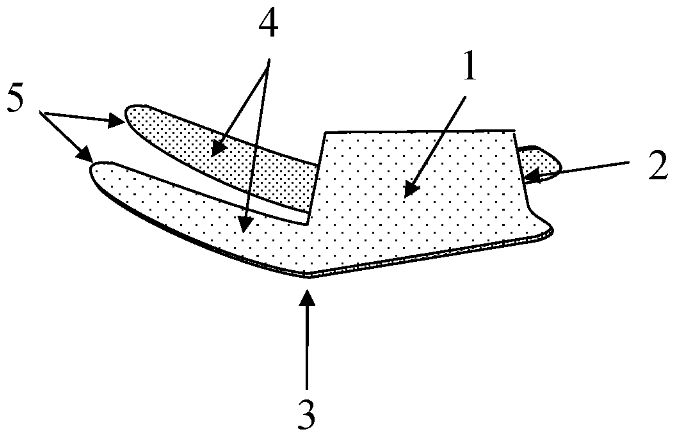
FIG. 2 is a side drawing demonstrating the second step in constructing an angular digital device for the distal interphalangeal joint with some embodiments of the inventive concepts disclosed herein.
Figure 3:
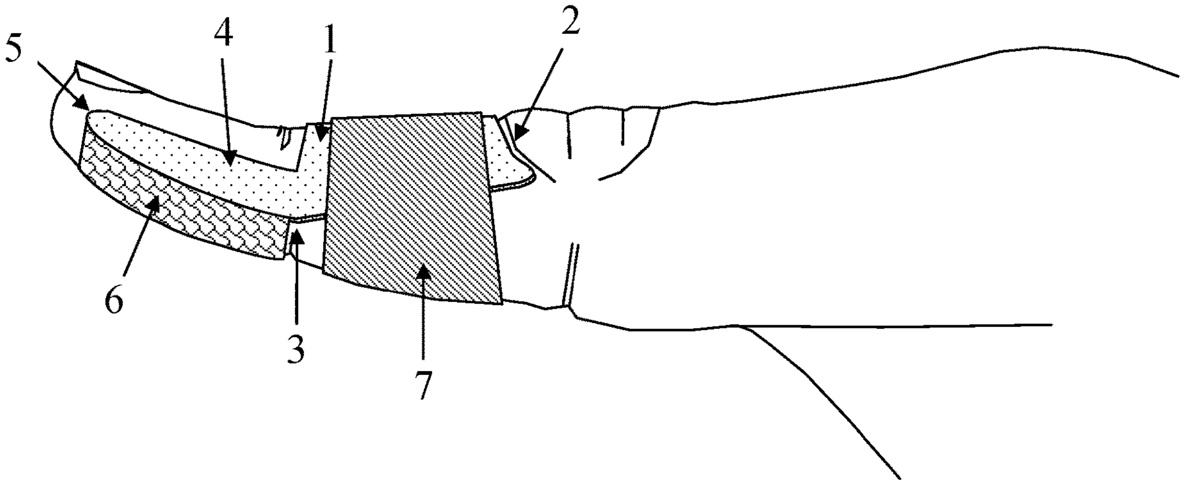
FIG. 3 is a side drawing of the completed construction of an angular digital device for the distal interphalangeal joint with the device applied to a digit with some embodiments of the inventive concepts disclosed herein.

By way of example and referring to FIGS. 1-3, one embodiment of the device may be created from a flat sheet of 0.04" polyester in the illustrated shape that has a proximal component 1 with fabric adhered on one or both sides of the polyester material and with the most proximal edge rounded on each side 2 to comfortably contour to the extension creases of a proximal interphalangeal joint of a digit. From this proximal component of the device arises one or more distal extensions 4 which arise from the proximal component at an angle 3 such that in subsequent construction steps this angle creates an apex volar angle at the level of the DIP joint of the digit. The distal end of the extension(s) 5 are rounded and of a length such that when applied to a digit does not cover the very tip of the digit but instead leaves the sensate tip exposed. A thin, flexible material 6 is secured to the distal extension(s) and is of a contour to support the volar aspect of the finger pad thereby creating an extension force on the DIP joint. Tape or a thin strap 7 is wrapped circumferentially at the level of the middle phalanx to secure the device to the digit.

Figure 4A:
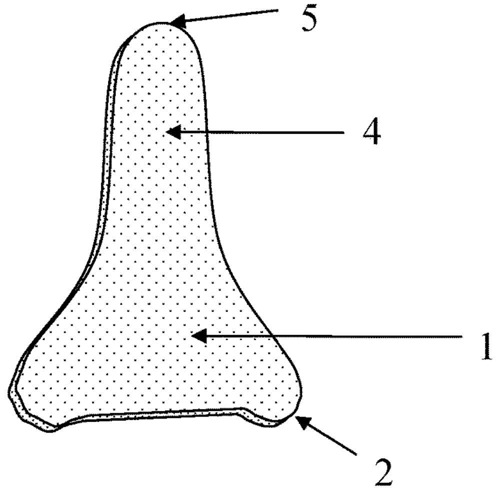
FIG. 4A is a top view drawing of the first step in constructing an additional embodiment of the inventive concepts disclosed herein of an angular digital device for the distal interphalangeal joint wherein a single distal extension arises from the proximal component.

By way of example and referring to FIG. 4A, one embodiment of the device may be created from a flat sheet of 0.04" polyester in the illustrated shape that has a proximal rigid component 1 with fabric optionally adhered on one or both sides of the polyester material and with the most proximal edge rounded on each side 2 to comfortably contour to the extension creases of a proximal interphalangeal joint of a digit. From this proximal rigid component of the device arises one distal extension 4 such that in the subsequent construction step (FIG. 4B), an apex volar angle at the level of the DIP joint of the digit is created 3. The distal end of the extension 5 is rounded and of a length such that when applied to a digit does not cover the very tip of the digit but instead leaves the sensate tip exposed.

Figure 4B:
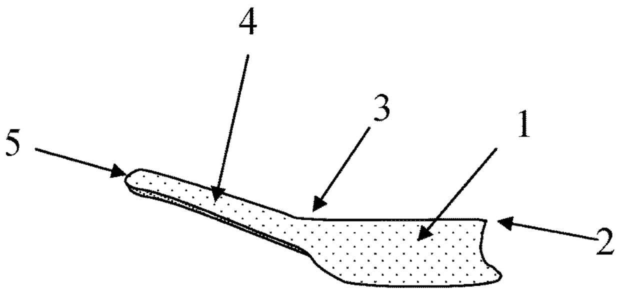
FIG. 4B is a side view drawing of the second step in construction of the embodiment depicted in FIG. 4A.

The device of FIG. 4B may alternatively be constructed using injection molding or additive manufacturing to achieve the same proximal component, distal extension, and angulation.

Figure 4C:
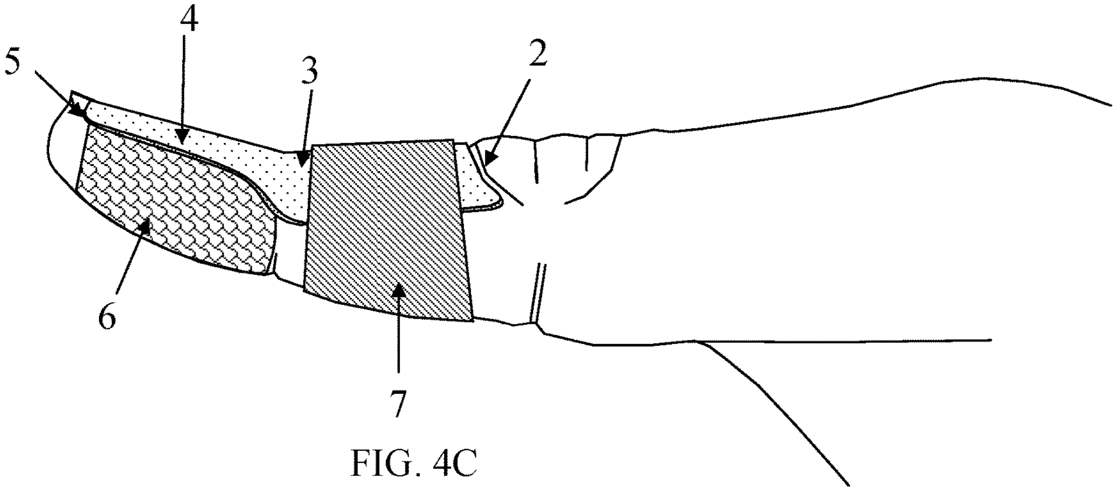
FIG. 4C is a side view drawing of the embodiment, wherein a thin, flexible material has been secured to the distal extension, and the embodied device is donned upon a digit.

By way of example and referring to FIG. 4C, a thin, flexible material 6 has been affixed to the distal extension 4 of the device of FIG. 4B and the device is illustrated in side view donned upon a digit. Tape or a thin strap 7 is wrapped circumferentially at the level of the middle phalanx to secure the device to the digit. The thin, flexible material supports the volar aspect of the finger pad when the device is donned thereby creating an extension force on the DIP joint.

By way of example and referring to FIG. 5A, one embodiment of the device may be created using a polymeric material formed by injection molding or additive manufacturing to create the rigid proximal component 1, distal extension 4, and angulation 3. FIG. 5B illustrates a cross-section of a thin, flexible material composed of a larger aperture 8 sized and shaped to fit the shape and size of the distal aspect of a digit, and a smaller aperture 9 shaped and sized to fit the distal extension 4 of the device illustrated in FIG. 5A. The smaller aperture 9 thus defines a longitudinal dorsal pocket extending along at least a portion of the length of the distal extension 4 and configured to receive the distal extension therein. When the distal extension is received within the dorsal pocket, the thin, flexible material is removably secured to the distal extension by engagement of the smaller aperture 9 with the distal extension 4, while permitting separation of the dorsal pocket from the distal extension when desired. FIG. 5C illustrates a side view of the completed device with the material of the smaller aperture 9 slid from distal to proximal upon the distal extension 4, and in so doing, a portion of the thin, flexible material defining the larger aperture 8 is positioned against the volar aspect of the distal extension. The device is illustrated donned upon a digit such that an extension force is created at the DIP joint.

By way of example and referring to FIGS. 6A-6E one embodiment of the device is illustrated. FIG. 6A illustrates a side view of the embodiment of the device created from a polymeric material using an injection mold process or additive manufacturing process to create a rigid proximal component 1, distal extension 4, and angulation 3. By way of example and referring to FIG. 6B, an end-on view is illustrated from distal to proximal while also showing the dorsal surface of the device. The geometry of the distal extension 4 is configured with side edges that taper inward from dorsal to palmar 10 such that an intermediate component may engage the distal extension in order to secure a thin, flexible material. FIG. 6C illustrates the intermediate component 11 with a complementary geometry to the distal extension such that it engages the distal extension and reversibly slides upon it from distal to proximal. FIG. 6D illustrates a top down view of the intermediate component 11, the proximal extent of which contains a circular hole 13 of a size and position to engage a convex contoured element 12 on the dorsal surface of the distal extension 4. Such engagement of the distal extension to the intermediate component with complementary geometry aids to secure the intermediate component to the distal extension. By way of example and referring to FIG. 6E, the distal extension and intermediate component are secured together such that the thin, flexible material supports the volar aspect of the finger pad when the device is donned thereby creating an extension force on the DIP joint. The tapered complementary geometry of the distal extension, and the intermediate component as illustrated in FIG. 6 is meant to be illustrative of only one of many possible geometries to engage these two components and is not limiting.

By way of example and referring to FIGS. 7A-D, an additional embodiment is illustrated. FIG. 7A illustrates a side view of the embodiment created from a polymeric material using an injection mold process or additive manufacturing process to create a rigid proximal component 1 with the most proximal edge rounded on each side 2 to comfortably contour to the extension creases of a proximal interphalangeal joint of a digit. By way of example and referring to FIG. 7B, an end-on view of the proximal component also illustrating the dorsal surface upon which a groove 14 is illustrated. The geometry of this groove is shaped such that an intermediate component 15 with a complementary shape may engage it. In this embodiment, when the intermediate rigid component 15 is engaged with the proximal rigid component 1, the intermediate rigid component defines a distal extension that is apex volarly angled and arises from the proximal rigid component. FIG. 7C is a cross-section view illustrating a thin, flexible material of a shape and size to fit the shape and size of the distal aspect of a digit, and secured upon the intermediate component. By way of example and referring to FIG. 7D, the two components are secured such that the thin, flexible material supports the volar aspect of the finger pad when the device is donned thereby creating an extension force on the DIP joint. The geometry of the groove, and the intermediate component as illustrated in FIG. 7 is meant to be illustrative of only one of many possible geometries to engage and secure these two components and is not limiting.

In certain embodiments formed by injection molding or additive manufacturing processes, and as illustrated in FIGS. 5-7, manufacturing efficiency and consistency may be improved and assembly steps reduced.

In certain embodiments where the thin, flexible material is reversibly secured, improvement in hygiene, simplicity of sizing, or improvement in extension force may be achieved by securing thin, flexible material of a different size, shape, or physical property, or of the same size, shape, and physical property but not worn and thus not soiled.

Terminology

"Volar" refers to the palmar or plantar surface of the hand
"Dorsal" refers to the side opposite the volar surface
"Proximal" refers to closer to the center axis of the body
"Distal" refers to further away from the center axis of the body
"Interphalangeal joints" referring to the joints between the proximal, middle, and distal phalanges of the digits of the hand
"Digit" a finger or thumb.

The invention claimed is:

1. A device configured to produce an extension force at the distal interphalangeal joint of a digit while not encumbering the middle interphalangeal joint of the digit, the device comprising:
- a proximal rigid portion configured to be secured to the middle phalanx and configured for spanning a longitudinal length of greater than one-half the length of the middle phalanx;
- a distal rigid portion comprising a single apex volarly angled distal extension arising from the proximal rigid portion and configured for providing an inclined angle at the joint between the proximal and distal rigid portions; and
- a thin flexible material secured to the single distal extension configured such that when the device is applied to the digit, a hyperextension force is created at the distal interphalangeal joint.

2. The device as recited in claim 1, wherein the thin flexible material is secured in a reversible manner to the distal rigid portion.

3. The device as recited in claim 2, wherein the thin flexible material is secured to the distal rigid portion via an intermediate rigid component.

4. The device as recited in claim 3, wherein the intermediate rigid component defines the single distal extension of the distal rigid portion when engaged with the proximal rigid portion.

5. The device as recited in claim 3, wherein the intermediate rigid component is configured to reversibly engage the proximal rigid portion.

6. The device as recited in claim 3, wherein the intermediate rigid component engages the proximal rigid portion via a complementary engagement geometry.

7. The device as recited in claim 3, wherein the intermediate rigid component is manufactured by injection molding or additive manufacturing.

8. The device as recited in claim 2, wherein the thin flexible material includes a dorsal longitudinal pocket that reversibly receives the single distal extension to secure the thin flexible material to the distal rigid portion.

9. The device as recited in claim 1, wherein one or more rigid components are manufactured by injection molding or additive manufacturing.

* * * * *